(12) United States Patent
Edwards et al.

(10) Patent No.: US 11,622,786 B2
(45) Date of Patent: Apr. 11, 2023

(54) PLANAR ALIGNMENT FOR ASYMMETRIC CUTTING MEMBERS

(71) Applicant: Gyrus ACMI, Inc., Southborough, MA (US)

(72) Inventors: Kevin Edwards, Olive Branch, MS (US); Jay Casey, Memphis, TN (US); Joel Willhite, Memphis, TN (US); Ahmad Alsaffar, Bartlett, TN (US)

(73) Assignee: GYRUS ACMI, INC., Westborough, MA (US)

( * ) Notice: Subject to any disclaimer, the term of this patent is extended or adjusted under 35 U.S.C. 154(b) by 379 days.

(21) Appl. No.: 16/365,962

(22) Filed: Mar. 27, 2019

(65) Prior Publication Data
US 2020/0305919 A1    Oct. 1, 2020

(51) Int. Cl.
*A61B 17/32* (2006.01)
*A61B 17/00* (2006.01)
(Continued)

(52) U.S. Cl.
CPC .... *A61B 17/32002* (2013.01); *A61B 10/0233* (2013.01); *A61B 10/0275* (2013.01);
(Continued)

(58) Field of Classification Search
CPC .......... A61B 17/32002; A61B 17/3205; A61B 17/32053; A61B 17/3209; A61B 2017/320028; A61B 2017/320024; A61B 2017/00982; A61B 10/02; A61B 10/0233; A61B 10/04; A61B 10/0275;
(Continued)

(56) References Cited

U.S. PATENT DOCUMENTS

| | | |
|---|---|---|
| 4,210,146 A | 7/1980 | Banko |
| 4,674,502 A | 6/1987 | Imonti |

(Continued)

FOREIGN PATENT DOCUMENTS

| | | |
|---|---|---|
| EP | 3714816 A1 | 9/2020 |
| JP | H0246842 A | 2/1990 |
| JP | 2003504090 A | 2/2003 |

OTHER PUBLICATIONS

"European Application Serial No. 20165426.6, Extended European Search Report dated Jul. 20, 2020", 13 pgs.

(Continued)

*Primary Examiner* — Richard G Louis
*Assistant Examiner* — Chima U Igboko
(74) *Attorney, Agent, or Firm* — Schwegman Lundberg & Woessner, P.A.

(57) ABSTRACT

Disclosed herein is a medical device. The medical device includes an outer tubular member and an inner tubular member. The outer tubular member has a distal end, an open window disposed at the distal end, and one or more dimples. The inner tubular member has a distal tip and one or more axial grooves. The inner tubular member is configured to be received within the outer tubular member. The one or more axial grooves and the one or more dimples are configured to align the distal tip of the inner tubular member with the open window of the outer tubular member. The open window of the outer tubular member and the distal tip of the inner tubular member are configured to cut tissue.

18 Claims, 6 Drawing Sheets

(51) Int. Cl.
*A61B 10/02* (2006.01)
*A61F 9/007* (2006.01)

(52) U.S. Cl.
CPC ............... *A61B 2010/0208* (2013.01); *A61B 2017/00982* (2013.01); *A61B 2017/320028* (2013.01); *A61B 2560/04* (2013.01); *A61F 9/00763* (2013.01)

(58) Field of Classification Search
CPC .... A61B 2010/0225; A61B 2010/0208; A61B 2560/04; A61F 9/007; A61F 9/00709; A61F 9/00736; A61F 9/00754; A61F 9/00763
See application file for complete search history.

(56) References Cited

U.S. PATENT DOCUMENTS

| | | | |
|---|---|---|---|
| 4,940,468 A * | 7/1990 | Petillo | A61F 9/00763 604/22 |
| 5,217,479 A * | 6/1993 | Shuler | A61B 17/32002 600/564 |
| 9,827,037 B2 | 11/2017 | Germain et al. | |
| 10,932,812 B2 * | 3/2021 | Lee | A61B 17/320016 |
| 2008/0183201 A1 * | 7/2008 | Berberich | A61B 17/32002 606/170 |
| 2011/0190660 A1 * | 8/2011 | Levy | A61B 10/0275 600/566 |
| 2012/0029354 A1 | 2/2012 | Mark et al. | |
| 2013/0046316 A1 | 2/2013 | Sullivan et al. | |
| 2014/0155923 A1 * | 6/2014 | Edwards | A61B 18/14 606/170 |
| 2015/0064165 A1 * | 3/2015 | Perry | A61K 31/728 424/94.67 |
| 2020/0187919 A1 * | 6/2020 | Long | A61B 10/0275 |

OTHER PUBLICATIONS

"European Application Serial No. 20165426.6, Response filed Mar. 30, 2021 to Extended European Search Report dated Jul. 20, 2020", 12 pgs.

"Japanese Application Serial No. 2020-54866, Notification of Reasons for Refusal dated May 17, 2021", 9 pgs.

"Japanese Application Serial No. 2020-54866, Examiners Decision of Final Refusal dated Oct. 4, 2021", w/ English Translation, 7 pgs.

* cited by examiner

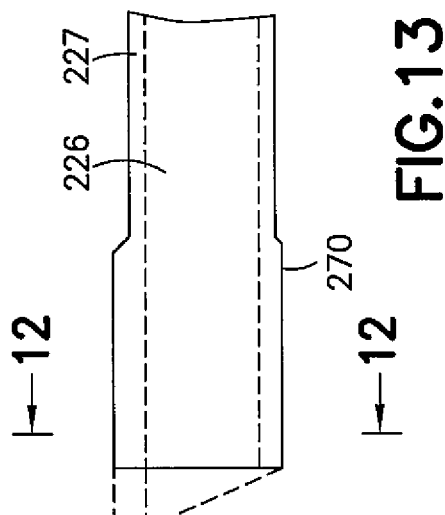
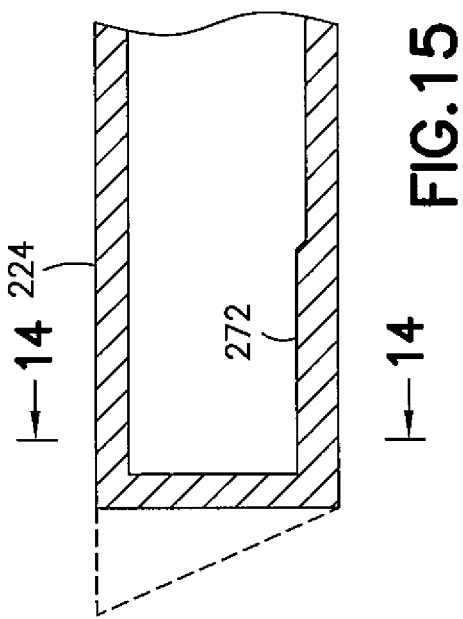
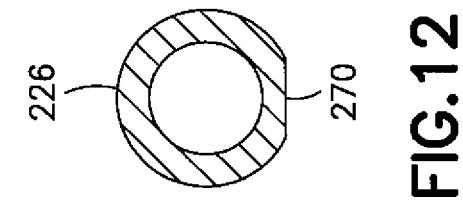
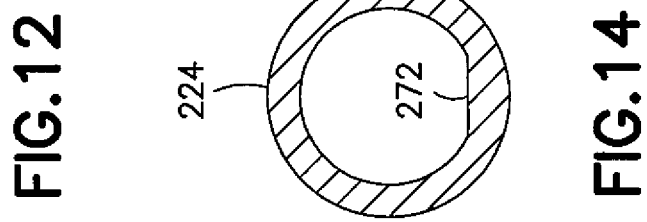

PLANAR ALIGNMENT FOR ASYMMETRIC CUTTING MEMBERS

BACKGROUND

Field of the Invention

The invention relates to a medical device and more specifically relates to planar alignment for cutting members of the medical device.

Brief Description of Prior Developments

Conventional surgical shavers having reciprocating blades can have symmetric or asymmetric cutting features. For inner members that have a symmetric tip shape about the cutting axis, planar alignment is generally not needed. However, for beveled or other asymmetric inner tip configurations, the inner and outer member must remain in plane to allow desired cutting action. This is further important if the outer member is rotating by some means to reorient the position of the cutting opening.

Accordingly, there is a need to provide improved and reliable medical device configurations having alignment features for the reciprocating blades.

SUMMARY

In accordance with one aspect of the invention, a medical device is disclosed. The medical device includes an outer tubular member and an inner tubular member. The outer tubular member has a distal end, an open window disposed at the distal end, and one or more dimples. The inner tubular member has a distal tip and one or more axial grooves. The inner tubular member is configured to be received within the outer tubular member. The one or more axial grooves and the one or more dimples are configured to align the distal tip of the inner tubular member with the open window of the outer tubular member. The open window of the outer tubular member and the distal tip of the inner tubular member are configured to cut tissue.

In accordance with another aspect of the invention, a medical device is disclosed. The medical device includes an outer tubular member and an inner tubular member. The outer tubular member has a distal end, a longitudinal axis, an open window disposed at the distal end, and a groove. The inner tubular member has a distal tip, an outer surface, an inner surface, and a pin disposed on the outer surface, the inner tubular member configured to be received within the outer tubular member. The pin of the inner tubular member is configured to mate with the groove of the outer tubular member to align the distal tip of the inner tubular member with the open window of the outer tubular member. The open window of the outer tubular member and the distal tip of the inner tubular member are configured to cut tissue.

In accordance with another aspect of the invention, a medical device including an outer member and an inner member. The outer member has a distal open window, an outer wall, and an inner wall. The inner member has a distal tip, an outer wall and an inner wall. The inner tubular member is configured to be received within the outer member. A distal section of the outer wall of the inner member and a distal section of the inner wall of the outer member are both configured to have flat surfaces to align the distal tip of the inner member with the distal open window of the outer member. The distal open window of the outer member and the distal tip of the inner member are configured to cut tissue.

BRIEF DESCRIPTION OF THE DRAWINGS

The foregoing aspects and other features of the invention are explained in the following description, taken in connection with the accompanying drawings, wherein:

FIG. 12 is a section view of an alternate embodiment of an inner blade tube of the medical device shown in FIG. 1 (section taken from view in FIG. 13);

FIG. 13 is a section view of the inner blade tube of the medical device shown in FIG. 12;

FIG. 14 is a section view of an alternate embodiment of an outer blade tube of the medical device shown in FIG. 1 (section taken from view in FIG. 15);

FIG. 15 is a section view of the outer blade tube of the medical device shown in FIG. 14.

DETAILED DESCRIPTION

Figure 1:
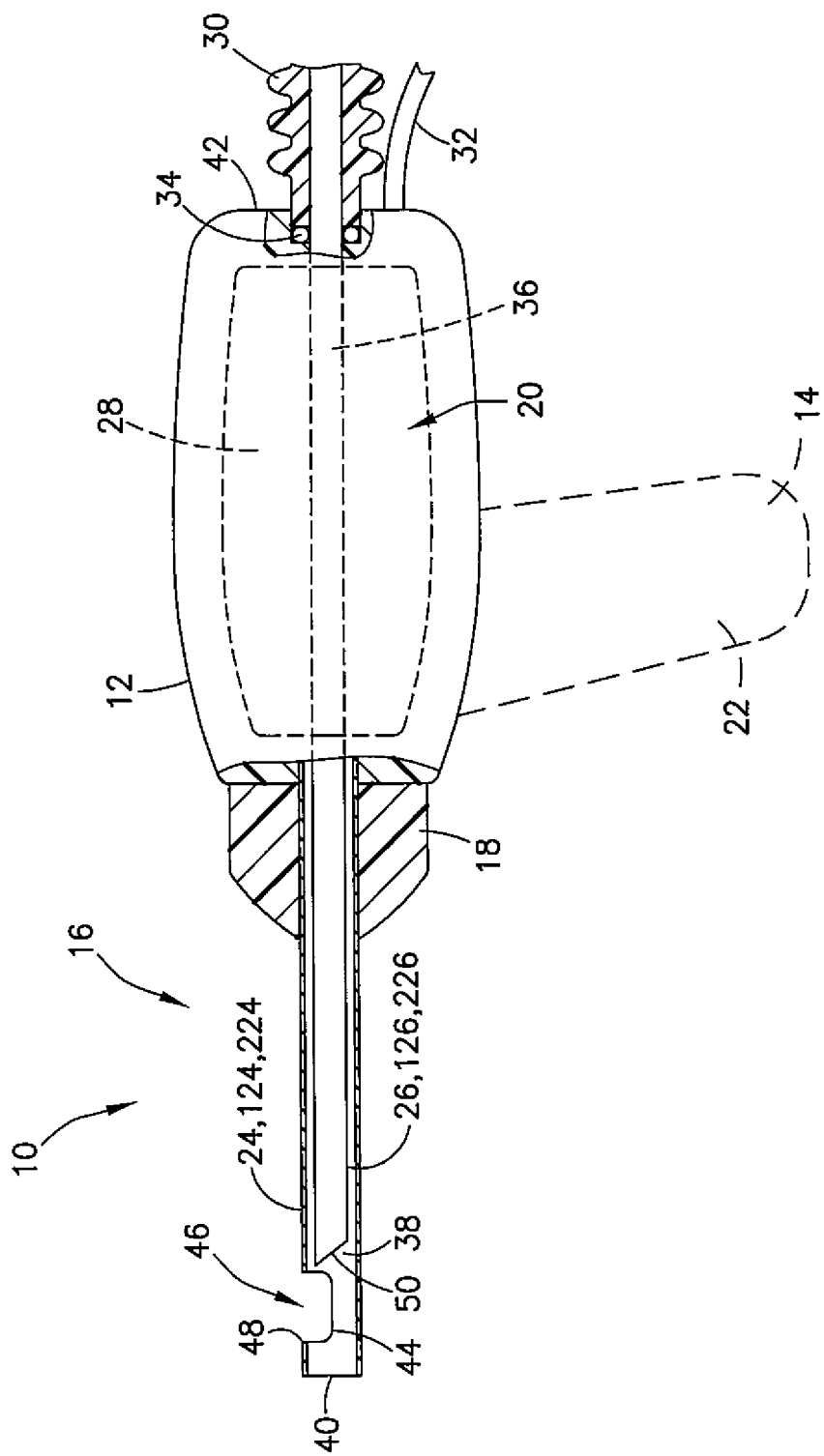
FIG. 1 is a side view of a medical device incorporating features of the invention.
Figure 3:
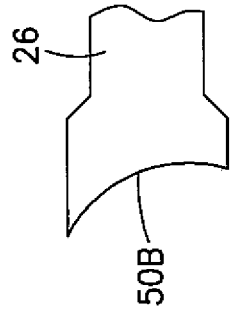
FIG. 3 is an alternate embodiment of a cutting tip used in the medical device shown in FIG. 1.
Figure 5:
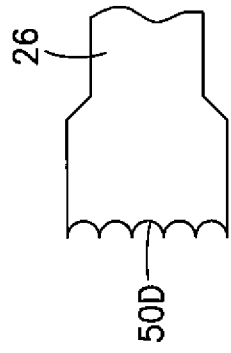
FIG. 5 is an alternate embodiment of a cutting tip used in the medical device shown in FIG. 1.
Figure 2:
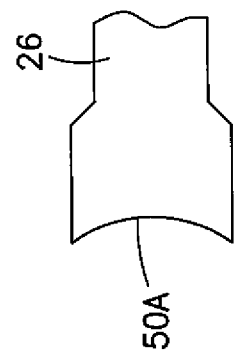
FIG. 2 is an alternate embodiment of a cutting tip used in the medical device shown in FIG. 1.
Figure 4:
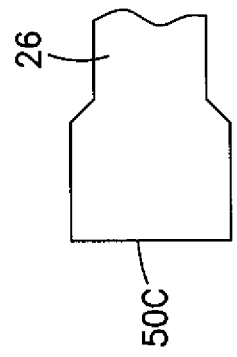
FIG. 4 is an alternate embodiment of a cutting tip used in the medical device shown in FIG. 1.

Referring to FIG. 1, there is shown a partial section side view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

According to various exemplary embodiments, the medical device 10 is generally configured for use in the removal of nasal polyps, sub-mucosal debulk of turbinates, and functional endoscopic sinus surgery (FESS).

The medical device 10, which may be a disposable debrider for example, comprises a housing 12 (which may have a pistol grip portion 14), a blade tube section 16, and a nosepiece 18. The nosepiece 18 may be a rotatable nosepiece and is between the housing 12 and the blade tube section 16. However, it should be noted that exemplary embodiments of the medical device may comprise any suitable configuration such as configurations having a nosecone coupled to an outer member (of the housing), or any other suitable curved or straight debrider configuration which may comprise an irrigation feature, for example. The blade tube section 16 of the device 10 can be configured with large and small shaver tubes, depending on anatomy and surgeon preference, and can also be adapted for bipolar or monopolar radio-frequency (RF) power. An external ESG (electrosurgical generator) may supply the RF power, for example.

The housing 12 comprises an interior cavity 20 sized and shaped to house actuation members of the device 10. Additionally, in some embodiments the optional pistol grip portion 14 may include an interior cavity 22 which can also be sized and shaped to house actuation members (or other hardware) of the device 10.

The blade tube section 16 comprises an outer blade tube 24 and an inner blade tube 26, and the medical device 10 further comprises a blade drive system 28 mounted within the cavity 20 (or mounted within the cavity 22) which is configured to drive the inner blade tube 26. It should be noted that in some embodiments, the blade tubes 24, 26 may comprise flexible and/or curved tubes.

Additionally, the medical device 10 comprises a connector 30 and a power cable 32. The connector (or suction connection) 30 is configured to connect to a suction tube or a vacuum source. The connector 30 includes a dynamic seal 34 mounted inside of the connector 30. The dynamic seal 34 is configured to provide a sealed interface between the connector 30 and an inner lumen 36 (via the outer surface of the inner blade tube 26) of the inner blade tube 26. The power cable 32 is configured to provide power to components(s) of the blade drive system 28.

The outer blade tube (or outer tubular member) 24 is (rotatably or fixedly) mounted to the housing 12 and acts as a static member. For example, according to various exemplary embodiments, the nosepiece 18 can be mounted to the outer blade tube 24 and can optionally rotate the outer blade tube 24 independent of the housing 12. The inner blade tube (or inner tubular member) 26 is slidably mounted inside the outer blade tube 24 (such that the inner blade tube 26 is slideably mounted within a lumen 38 of the outer blade tube 24).

The inner blade tube 26 is configured to be forced distally [i.e. towards the distal end 40] or proximally [i.e. towards the proximal end 42] by the blade drive system 28. The outer blade tube 24 comprises an opening (or open window) 44 proximate the distal end 40 which forms a cutting window 46 for the medical device 10. The cutting window 46 is formed by a cutting edge 48 of the outer blade tube (i.e. the distal edge of the opening 44) and a cutting tip 50 of the inner blade tube 26. The reciprocal motion of the inner blade tube 26 provides for the cutting tip 50 to reciprocate relative to the cutting edge 48 to perform tissue cuts (i.e. by bringing the cutting tip 50 into alignment and out of alignment with the opening 44 of the outer blade tube 24). In the embodiment shown in FIG. 1, the cutting edge is at the cylindrical face portion of the cutting window 46. However in alternate embodiments, the cutting edge may be provided at any suitable location along the distal end 40.

It should be noted that although various exemplary embodiments of the invention have been described in connection with the cutting tip 50 comprising an angled straight edge configuration, alternate embodiments may comprise other suitable configurations. For example, FIGS. 2-5 illustrate alternate embodiments for the cutting tip 50 (see cutting tips 50A, 50B, 50C, 50D).

Figure 7:
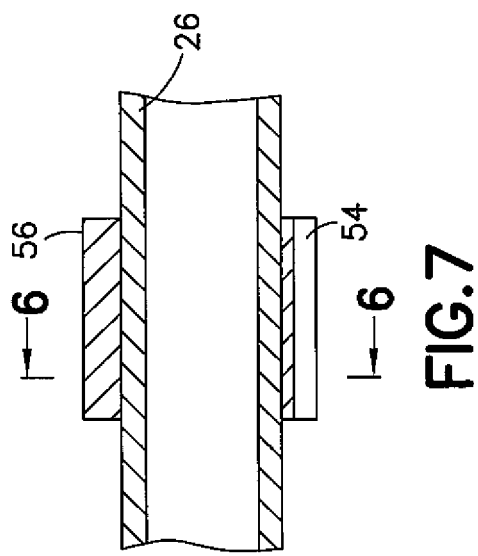
FIG. 7 is a section view of the inner blade tube of the medical device shown in FIG. 1.
Figure 8:
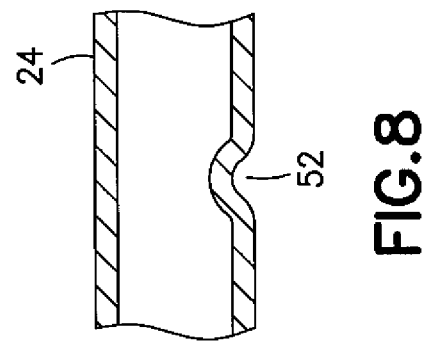
FIG. 8 is a section view of the outer blade tube of the medical device shown in FIG. 1.
Figure 6:
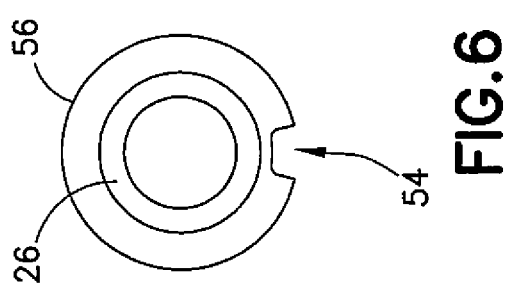
FIG. 6 is a section view of the inner blade tube of the medical device shown in FIG. 1 (section taken from view in FIG. 7)

Referring now also to FIGS. 6-8, an exemplary embodiment is shown which provides for planarly aligning the non-moving (outer) member 24 with the reciprocating (inner) member 26 of the reciprocating cutting instrument.

In the embodiment shown in FIGS. 6-8, a formed dimple 52 in the outer member 24, and an axial groove 54 in the inner member 26 are provided. The axial groove 54 can be provided at a collar 56 affixed (or otherwise coupled) to the inner member 26. However, in alternate embodiments, the axial groove could be provided at the outer surface of the inner member 26. According to various exemplary embodiments, the axial groove 54 can be any length longer than the cutting stroke of the inner member 26, and is configured to receive the dimple 52 when the inner member 26 is inserted into the outer member 24. The axial groove 54 and dimple 52 are sized to prevent rotation of the inner member 26 independent of the outer member 24. With the receiving of the dimple 52 within the axial groove 54, any rotation between the inner member 26 and the outer member 24 is prevented and a planar alignment is therefore provided between the inner member 26 and the outer member 24. The planar alignment between the inner member 26 and the outer member 24 allows for a desired position of the cutting tip 50 relative to the cutting edge 48 (by preventing rotation of the inner member 26 [along a longitudinal axis of the inner member 26] relative to the outer member 24).

According to various exemplary embodiments, the axial groove features can be provided in more than one location so long as it remains adjacent to one of more of the dimple features, and may also be placed at any point along the axis of the blade tube section 16 so long as it remains adjacent the dimple feature. Additionally, in some embodiments, the dimple may comprise an elongated shape extending in the axial direction so as to form an axial dimple.

Figure 10:
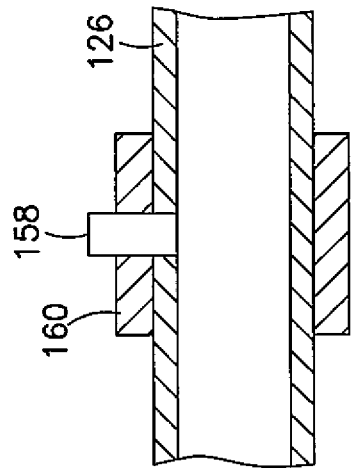
FIG. 10 is a section view of an alternate embodiment of an inner blade tube of the medical device shown in FIG. 1.
Figure 9:
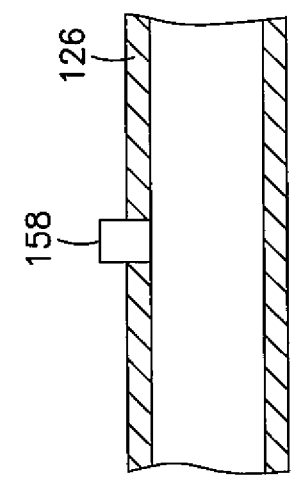
FIG. 9 is a section view of an alternate embodiment of an inner blade tube of the medical device shown in FIG. 1.
Figure 11:
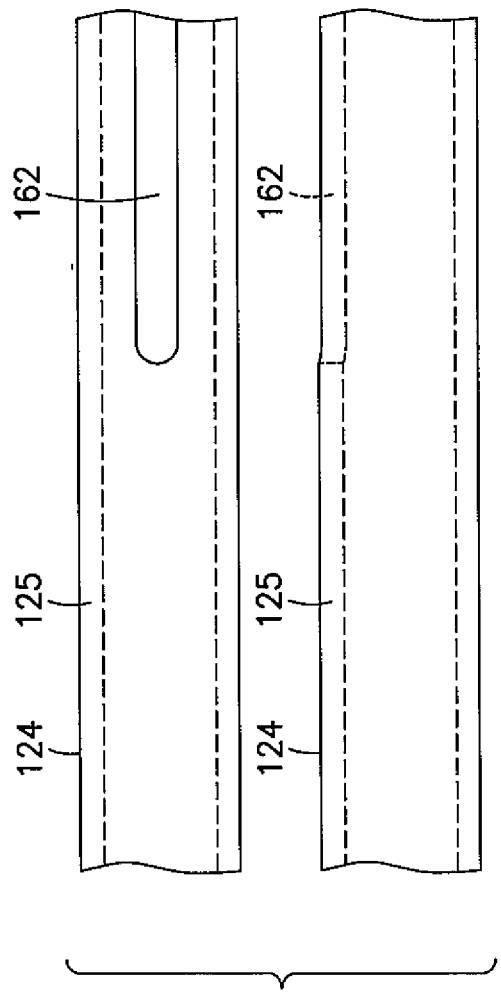
FIG. 11 is a section view of alternate embodiments of an outer blade tube of the medical device shown in FIG. 1.

Referring now also to FIGS. 9-11, another exemplary embodiment is shown which provides for planarly aligning a non-moving (outer) member 124 with a reciprocating (inner) member 126 of the reciprocating cutting instrument 10. The non-moving (outer) member 124 is similar to the non-moving (outer) member 24, and the reciprocating (inner) member 126 is similar to the reciprocating (inner) member 26. However, in the embodiment shown in FIGS. 9-11, a pin 158 is affixed (or coupled) to the outer surface of the inner tubular member 126 (see FIG. 9) and/or affixed (or coupled) to one or more collars 160 that are affixed (or coupled) to the inner tubular member 126 (see FIG. 10). A groove 162 in the outer member 124 is sized and shaped to allow for mating with the pin 158. The groove 162 can be partially or completely through a wall section 125 of the outer tubular member 124, and may also include a collar (not shown) affixed to the outside of the outer member. The groove 162 can also be formed completely through both the wall section 125 of the outer member 124 and collar (not shown), or completely through the wall section 125 of the outer member 124 and partially through the collar (not shown).

According to various exemplary embodiments, the mating groove feature 162 can be any length longer than the cutting stroke of the inner member 126, and is configured to receive the pin 158 when the inner member 126 is inserted into the outer member 124. The groove 162 and the pin 158 are sized to prevent rotation of the inner member 126 independent of the outer member 124. With the receiving of the pin 158 within the groove 162, any rotation between the inner member 126 and the outer member 124 is prevented and a planar alignment is therefore provided between the inner member 126 and the outer member 124. The planar alignment between the inner member 126 and the outer member 124 allows for a desired position of the cutting tip 50 relative to the cutting edge 48 (by preventing rotation of the inner member 126 [along a longitudinal axis of the inner member 126] relative to the outer member 124).

According to various exemplary embodiments, the mating groove features can be provided in more than one location so long as it is adjacent to the pin or pins, and be placed at any point along the axis of the device so long as adjacent to pin.

Referring now also to FIGS. 12-15, another exemplary embodiment is shown which provides for planarly aligning a non-moving (outer) member 224 with a reciprocating (inner) member 226 of the reciprocating cutting instrument 10. The non-moving (outer) member 224 is similar to the non-moving (outer) member 24, and the reciprocating (inner) member 226 is similar to the reciprocating (inner) member 26. However, in the embodiment shown in FIGS. 12-15, a machined flat section 270 is provided on the tip (or distal end) of the inner member 226, and a mating general 'circle D' shaped feature 272 is provided on an inner surface of the outer member 224. The inner member 226 fits concentrically inside the bore of outer member 224 in close diametric proximity along the expanded bearing section at the distal tip of the device. The wall section 227 of the inner member 226 can be decreased proximal of the distal bearing to provide relief clearance between the inside diameter (ID) of the outer member 224 and the outside diameter (OD) of the inner member 226.

According to various exemplary embodiments, the outer member feature 272 can be any length longer than the cutting stroke of the inner member 226, and is configured to receive the flat section 270 when the inner member 226 is inserted into the outer member 224. The flat section 270 and the 'circle D' shaped features 272 are sized and shaped to prevent rotation of the inner member 226 independent of the outer member 224. Since the 'circle D' shaped feature 272 and the flat section 270 (which provide bearing sections of the distal tips of the outer and inner members 224, 226) are in close fit, the inner member 226 is constrained from rotating about its axis independently of the outer member 224.

With the receiving of the flat section 270 within the 'circle D' shaped feature 272, any rotation between the inner member 226 and the outer member 224 is prevented and a planar alignment is therefore provided between the inner member 226 and the outer member 224. The planar alignment between the inner member 226 and the outer member 224 allows for a desired position of the cutting tip 50 relative to the cutting edge 48 (by preventing rotation of the inner member 226 [along a longitudinal axis of the inner member 226] relative to the outer member 224).

According to various exemplary embodiments, the outer member feature can be provided in more than one location, and be placed at any point or points along the axis of the device. The outer member can be a single piece or multiple pieces in which the wall of the outer tubular member and the section comprising the 'circle D' shaped feature are affixed by welding or other suitable means.

Technical effects of any one or more of the exemplary embodiments provide significant advantages over conventional configurations by planarly aligning a non-moving (outer) member with a reciprocating (inner) member of a reciprocating cutting instrument. Another technical effect of the various exemplary embodiments is that the alignment features can be used with both straight and curved devices.

Figure 16:
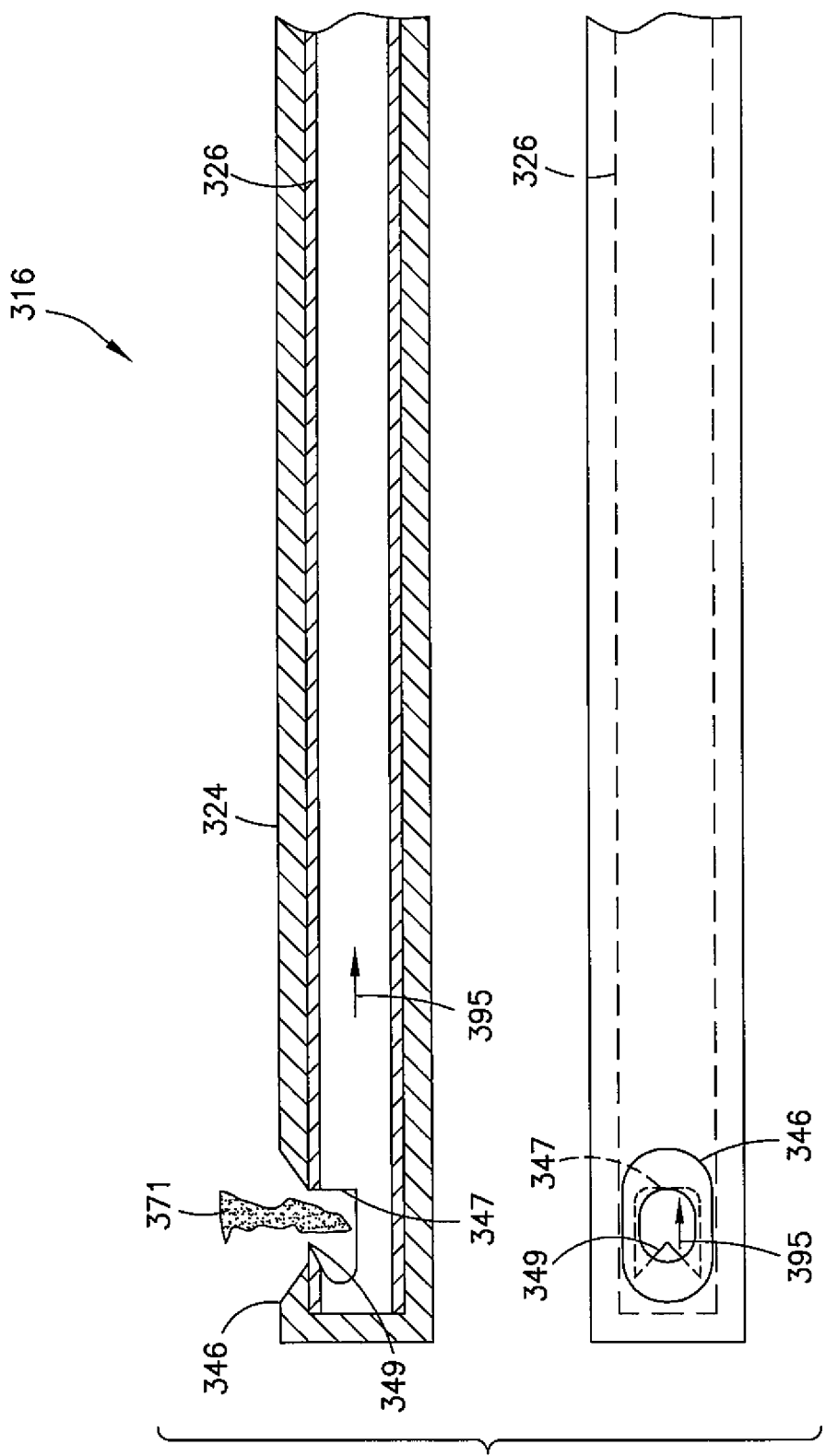
FIG. 16 is a section view and a top plan view of an alternate blade tube section used in the medical device shown in FIG. 1.

While various exemplary embodiments of the invention have been described in connection with a blade tube section 16 having a cutting edge 48 at the cutting window 46 of the outer blade tube 24, 124, 224, other configurations may be provided. For example, an alternate embodiment of a blade tube section 316 is shown in FIG. 16 (illustrating a cross-section view [top] and a top plan view [bottom]). Similar to the blade tube section 16, the blade tube section 316 comprises an outer blade tube 324 and an inner blade tube 326 configured to be driven by the blade drive system 28. However in this embodiment, the inner blade tube 326 comprises a cutting window 347 and a cutting edge 349. The cutting window 347 is configured to be aligned with the window 346 of the outer blade tube 324 such that the cutting is provided when tissue 371 extends through the windows 346, 347 and a backwards motion of the inner blade tube 326 (towards the proximate end [see arrow 395]) causes the cutting edge 349 to cut through the tissue 371.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising: an outer tubular member having a distal end, an open window disposed at the distal end, and one or more dimples; and an inner tubular member having a distal tip and one or more axial grooves, the inner tubular member configured to be received within the outer tubular member; wherein the one or more axial grooves and the one or more dimples are configured to align the distal tip of the inner tubular member with the open window of the outer tubular member, and wherein the open window of the outer tubular member and the distal tip of the inner tubular member are configured to cut tissue.

A medical device as above wherein the distal tip of the inner tubular member comprises an asymmetric distal tip.

A medical device as above wherein the one or more dimples of the outer tubular member comprise one or more axial dimples.

A medical device as above wherein the inner tubular member is configured to reciprocate relative the outer tubular member.

A medical device as above wherein the medical device is configured to cut tissue when the inner tubular member reciprocates.

A medical device as above further comprising a collar connected to the inner tubular member, wherein the collar comprises the one or more axial grooves.

In another exemplary embodiment, a medical device comprising: an outer tubular member having a distal end, a longitudinal axis, an open window disposed at the distal end, and a groove; and an inner tubular member having a distal tip, an outer surface, an inner surface, and a pin disposed on the outer surface, the inner tubular member configured to be received within the outer tubular member; wherein the pin of the inner tubular member is configured to mate with the groove of the outer tubular member to align the distal tip of the inner tubular member with the open window of the outer tubular member, and wherein the open window of the outer tubular member and the distal tip of the inner tubular member are configured to cut tissue.

A medical device as above wherein the groove extends along a direction of the longitudinal axis.

A medical device as above wherein the distal tip of the inner tubular member comprises an asymmetric distal tip.

A medical device as above wherein the medical device is configured to cut tissue when the inner tubular member reciprocates relative the outer tubular member.

A medical device as above further comprising a collar connected to the inner tubular member, wherein the pin is at the collar.

A medical device as above wherein the groove is at a wall section of the outer tubular member.

In another exemplary embodiment, a medical device comprising: an outer member having a distal open window, an outer wall, and an inner wall; and an inner member having a distal tip, an outer wall and an inner wall, the inner tubular member configured to be received within the outer member; wherein a distal section of the outer wall of the inner member and a distal section of the inner wall of the outer member are both configured to have flat surfaces to align the distal tip of the inner member with the distal open window of the outer member, and wherein the distal open window of the outer member and the distal tip of the inner member are configured to cut tissue.

A medical device as above wherein the distal tip of the inner member comprises an asymmetric distal tip.

A medical device as above wherein the inner member is configured to reciprocate relative the outer member.

A medical device as above wherein the medical device is configured to cut tissue when the inner member reciprocates.

A medical device as above wherein the flat surfaces are configured to prevent rotation between the inner member and the outer member.

A medical device as above wherein the flat surface of the outer member is at an inner wall section of the outer member.

A medical device as above wherein the flat surface of the inner member is at an outer wall section of the inner member.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
   a housing extending from a proximal end to a distal end;
   a rotatable nosepiece mounted to the distal end of the housing, wherein the nosepiece is rotatable relative to the housing; and
   a blade tube section extending distally from a distal end of the nosepiece, wherein the blade tube section comprises:
      an outer blade tube having a distal end, an open window disposed at the distal end and extending through an outer wall of the outer blade tube, and one or more dimples, wherein the outer blade tube is fixedly coupled to the nosepiece such that rotation of the nosepiece causes a corresponding rotation of the outer blade tube relative to the housing; and
      an inner blade tube having a distal tip and one or more axial grooves, the inner blade tube configured to be received within the outer blade tube;
      wherein the one or more dimples and the one or more axial grooves are disposed in the blade tube section distal to the nosepiece and the housing;
      wherein the one or more axial grooves and the one or more dimples are configured to align the distal tip of the inner blade tube with the open window of the outer blade tube and to prevent rotation of the inner blade tube independent of the outer blade tube, and wherein the open window of the outer blade tube and the distal tip of the inner blade tube are configured to cut tissue.

2. A medical device as in claim 1 wherein the distal tip of the inner blade tube comprises an asymmetric distal tip.

3. A medical device as in claim 1 wherein the one or more dimples of the outer blade tube comprise one or more axial dimples.

4. A medical device as in claim 1 wherein the inner blade tube is configured to reciprocate relative the outer blade tube.

5. A medical device as in claim 1 wherein the medical device is configured to cut tissue when the inner blade tube reciprocates.

6. A medical device as in claim 1 further comprising a collar connected to the inner blade tube, wherein the collar comprises the one or more axial grooves.

7. A medical device comprising:
   a housing extending from a proximal end to a distal end;
   a rotatable nosepiece mounted to the distal end of the housing, wherein the nosepiece is rotatable relative to the housing; and
   a blade tube section extending distally from a distal end of the nosepiece, wherein the blade tube section comprises:
      an outer blade tube having an outer surface, an inner surface, a distal end, a longitudinal axis, an open window disposed at the distal end and extending through the outer and inner walls of the outer blade tube, and an axially extending groove, wherein the outer blade tube is fixedly coupled to the nosepiece such that rotation of the nosepiece causes a corresponding rotation of the outer blade tube relative to the housing; and
      an inner blade tube having a distal tip, an outer surface, an inner surface, and a pin disposed on the outer surface of the inner blade tube, the inner blade tube configured to be received within the outer blade tube;
      wherein the axially extending groove and the pin are disposed in the blade tube section distal to the nosepiece and the housing;
      wherein the pin of the inner blade tube is configured to mate with the groove of the outer blade tube to align the distal tip of the inner blade tube with the open window of the outer blade tube and to prevent rotation of the inner blade tube independent of the outer blade tube, and wherein the open window of the outer blade tube and the distal tip of the inner blade tube are configured to cut tissue.

8. A medical device as in claim 7 wherein the groove extends along a direction of the longitudinal axis.

9. A medical device as in claim 7 wherein the distal tip of the inner blade tube comprises an asymmetric distal tip.

10. A medical device as in claim 7 wherein the medical device is configured to cut tissue when the inner blade tube reciprocates relative the outer blade tube.

11. A medical device as in claim 7 further comprising a collar connected to the inner blade tube, wherein the pin is at the collar.

12. A medical device as in claim 7 wherein the groove is at a wall section of the outer blade tube.

13. A medical device comprising:
- a housing extending from a proximal end to a distal end;
- a rotatable nosepiece mounted to the distal end of the housing, wherein the nosepiece is rotatable relative to the housing; and
- a blade tube section extending distally from a distal end of the nosepiece, wherein the blade tube section comprises:
  - an outer blade tube having an outer wall, an inner wall, and a distal open window extending through the outer and inner walls of the outer blade tube, wherein the outer blade tube is fixedly coupled to the nosepiece such that rotation of the nosepiece causes a corresponding rotation of the outer blade tube relative to the housing; and
  - an inner blade tube having a distal tip, an outer wall and an inner wall, the inner blade tube configured to be received within the outer blade tube;
  - wherein a distal section of the outer wall of the inner blade tube and a distal section of the inner wall of the outer blade tube both comprise flat surfaces configured to align the distal tip of the inner blade tube with the distal open window of the outer blade tube, and wherein the distal open window of the outer blade tube and the distal tip of the inner blade tube are configured to cut tissue;
  - wherein the flat surfaces are disposed in the blade tube section distal to the nosepiece and the housing; and
  - wherein the flat surfaces are configured to prevent rotation between the inner blade tube and the outer blade tube.

14. A medical device as in claim 13 wherein the distal tip of the inner blade tube comprises an asymmetric distal tip.

15. A medical device as in claim 13 wherein the inner blade tube is configured to reciprocate relative the outer blade tube.

16. A medical device as in claim 13 wherein the medical device is configured to cut tissue when the inner blade tube reciprocates.

17. A medical device as in claim 13 wherein the flat surface of the outer blade tube is at an inner wall section of the outer blade tube.

18. A medical device as in claim 13 wherein the flat surface of the inner blade tube is at an outer wall section of the inner blade tube.

* * * * *